United States Patent [19]

Ricotti et al.

[11] 4,404,279

[45] Sep. 13, 1983

[54] METHOD OF CULTURING HYBRIDOMAS

[75] Inventors: Giulia C. B. A. Ricotti, Hoofddorp; Willem P. Zeijlemaker, Roelofarendsveen, both of Netherlands

[73] Assignee: Stichting Vrienden van de Stichting Dr. Karl Landsteiner, Amsterdam, Netherlands

[21] Appl. No.: 229,272

[22] Filed: Jan. 28, 1981

[30] Foreign Application Priority Data

Jan. 29, 1980 [NL] Netherlands .................. 8000527

[51] Int. Cl.$^3$ .................. C12P 21/00; C12N 1/00; C12N 1/38; C12N 15/00
[52] U.S. Cl. .................................. 435/68; 435/243; 435/244; 435/172
[58] Field of Search ............... 435/240, 243, 68, 948, 435/244, 172; 424/85

[56] References Cited

PUBLICATIONS

Astaldi et al.; Biol. Abstr. 71, 17274 (1981), Abstr. of Astaldi et al.; J. Immunol. 125, 1411-1414 (1980).
Nature, vol. 256, Aug. 7, 1975, pp. 494-497 G. Kohler et al.
Chemical Abstracts, vol. 89, No. 11, Sep. 11, 1978, p. 292, No. 87749K Columbus, Ohio, E. A. Jaffe et al. and J. Exp. Med. 1978, 147(6), 1779-1791.
Chemical Abstracts, vol. 91, No. 7, Aug. 13, 1979, p. 433, No. 53616R, Columbus Ohio, F. Grinnell et al. and Cell (Cambridge, Mass.) 1979, 17(1) 177-129.

*Primary Examiner*—Alvin E. Tanenholtz
*Assistant Examiner*—James Martinell
*Attorney, Agent, or Firm*—Kane, Dalsimer, Kane, Sullivan and Kurucz

[57] ABSTRACT

The invention relates to a method for increasing the hybridization of cells in vitro and for increasing the production and secretion of substances, formed by such cell hybrids by adding endothelial cells and/or the supernatant of endothelial cells to a hybrid culture. In particular the invention is concerned with a method for increasing the production of monoclonal antibodies in vitro by means of a hybridoma technique by adding endothelial cells and/or the supernatant of endothelial cells to a hybridoma culture. Usually human endothelial cells and/or the supernatant of human endothelial cells are used. Finally the invention relates to endothelial cells and/or the supernatant of endothelial cells for use for increasing the hybridization of cells in vitro and for increasing the production and secretion of substances, formed by such cell hybrids, and for increasing the production of monoclonal antibodies in vitro.

13 Claims, No Drawings

METHOD OF CULTURING HYBRIDOMAS

BACKGROUND OF THE INVENTION

1. Field of the Invention

The invention relates to a method for increasing the hybridization in cells in vitro and for increasing the production and secretion of substances, formed by such cell hybrids, a method for increasing the production of monoclonal antibodies in vitro by means of a hybridoma technique and endothelial cells and/or supernatant of endothelial cells.

2. Brief Description of the Prior Art

The introduction of hybrids between two different cells appears to be successful in the in vitro synthesis and secretion of various cell products. Furthermore, this technique is largely used in gene mapping. It was shown (Köhler, G. and Milstein, C: Nature, Vol. 256, p. 495,-1975-) to permit the production of monoclonal antibodies (thus pure antibodies of one specificity directed to a single antigenic determinant) rather than a mixture of antibodies thus with several (undesired) specificities, as obtained by conventional immunization in vivo. Futhermore, by means of the hybridization of human cells the production of human monoclonal antibodies may be obtained.

The technique of the production of monoclonal antibodies comprises essentially three steps:

(1) Fusion of myeloma cell line cells with lymphocytes obtained from an animal immunized with the desired antigen in order to obtain hybridomas secreting the desired antibodies and growing permanently in vitro.

(2) Selection of the desired hybridoma clone by means of culturing at the single cell level (limiting dilution).

(3) Keeping alive, splitting and maintaining the function of the selected monoclonal cell line in vitro during a prolonged time.

It appeared that all these steps present a number of problems:

(1) The fusion is usually performed at non constant and relatively low efficiency (number of hybrids obtained is usually too low).

(2) The limiting dilution requires the presence of "feeder" cells; said often provide a strongly varying activity.

(3) The survival of hybridomas obtained by fusion of human cells with mouse-myeloma cells is often very limited in time.

The above-mentioned steps and problems are in common with all the hybrids between different cells.

SUMMARY OF THE INVENTION

The invention provides now a method for increasing the hybridization of cells in vitro and for increasing the production and secretion of substances formed by such cell hybrids, characterized in that one adds to a hybrid culture human endothelial cells and/or the supernatant of human endothelial cells.

In particular the invention provides a method for increasing the production of monoclonal antibodies in vitro by means of a hybridoma technique, wherein one adds to a hybridoma culture human endothelial cells and/or the supernatant of human endothelial cells. By using the method of the invention the above-mentioned disadvantages are efficiently removed.

According to the invention the number of cells producing monoclonal antibodies in vitro is significantly increased.

DETAILED DESCRIPTION OF THE INVENTION

Based on the assumption that a successful cell fusion (see example 2), growth at the single cell level in vitro (see example 3), keeping alive, splitting and maintaining the function of hybridomas during a prolonged time (see example 4) is largely dependent upon the presence of factor(s) produced by cells, we attempted to identify such factor(s).

We found that endothelial cells and the supernatant of such endothelial cells, endothelial cells themselves or the supernatant of endothelial cells after addition do:

(1) increase the number of hybrids obtained after fusion, (2) permit high and constant efficiency of number of clones obtained by limiting dilution, (3) keep alive, split and maintain the function of hybridomas in vitro during a prolonged time.

Without intending to be bound to any mechanism of action, there is evidence that the activity of endothelial cells is mediated by factor(s) produced or released during culture. Although the chemistry of these factor(s) is not yet known, it is unlikely that they are prostaglandins (see example 5).

These factor(s) produced by endothelial cells may potentially also help the growth of hybrids between cells different from myeloma cells and lymphocytes (such as hepatoma cells and liver cells, fibroblast and lymphocytes, etc.). and the growth of cells difficult to grow in vitro such as bone marrow cells. It is shown that the endothelial cell supernatant induces and/or enhances the growth of different colonies of human bone marrow cells in vitro (see example 6).

The induction of enhancement of human bone marrow cells has also been described for granulopoiesis (c.f. Knudtzon, S. and Mortsensen, B. T.: Blood, Vol. 46, p. 537,-1975-).

It should be understood that according to the invention a hybridoma culture is used, which is obtained by fusion of myeloma cell line cells and lymphocytes, derived from animals or human beings, which are immunized with the desired antigens.

The invention will now be illustrated by the following examples:

EXAMPLE 1

Culture of human endothelial cells and production of human endothelial cell supernatant, termed "HECS" (Human Endothelial Culture line supernatant).

Human endothelial cells are isolated and cultured according to the method originally described by Joffe, E. A. et al., J. Clin. Invest. 52, p. 2745-2756 (1973).

Human umbillical cord veins are washed with 0,1 M phosphate buffer (PH7.4) containing 0.9% NaCl. Subsequently the vessel is filled with phosphate buffer, dissolved therein trypsin (0,5 gr/l) and EDTA (1,2 gr/l). After 15 minutes incubation at 37° C. the incubation medium is removed and the vessel wall is filled again with buffer. After slight traumatisation of the vessel wall the buffer solution was collected and pooled with the first effluent. To this cell suspension 5 ml. of growth medium (GM) is added. This medium consists of:

—35% $RPMI_{(1640)}$ Hepes
—35% $M_{(199)}$ Hanks balanced salts

—30% pooled human serum obtained from 18 normal human donors.

After centrifugation (5 min. 200 gr.) a small white pellet is obtained which is resuspended in 10 ml of the above growth medium. The cells thus obtained are plated in tissue culture flasks. After 5-6 days a confluent monolayer of cells is obtained. This monolayer is incubated with buffered trypsin EDTA for 3-5 minutes. The detached cells are washed according to the above-mentioned procedure and again inoculated in tissue culture flasks with a split ratio of 1-4 or 1-5. The cultured cells are identified as endothelial cells by the following criteria:

(1) the cells show a density dependent regulation of growth (2) using immunofluorescence the presence of factor VIII related antigen and fibronectine could be demonstrated (3) using electron microscopy the presence of Weibel Palade bodies could be demonstrated.

Cultures of endothelial cells are maintained in the presence of growth medium which is refreshed twice a week. The medium which for 2-4 days is on top of confluent cells (the endothelial cell supernatant) is collected and used.

Alternatively: when endothelial cells are confluent they may be refreshed with culture medium containing Fetal Calf Serum (FCS) in plane of growth medium, to avoid the presence of human serum in the supernatant.

EXAMPLE 2

Increase of fusion efficiency by means of human endothelial cell supernatant "HECS).

Mouse myeloma cells are fused with immunized mouse spleen cells or human lymphocytes in the presence of polyethylene glycol according to the method of Galfre, G. et al., Nature, Vol 266, p. 550 (1977) or Kennet, R. H. et al. in: Current Topics in Microbiology and Immunology, Vol. 81, p. 77 (1978); the fused cells are washed and dispensed into 96 wells tissue culture plate containing "HECS" or as control normal medium. After 10-20 days colonies of hybrid clones become evident.

The following two tables illustrate the induction of a higher number of hybrids induced by "factor".

TABLE A

| | mouse myeloma cells × mouse lymphocytes | | | |
|---|---|---|---|---|
| | Fusion 1 | | Fusion 2 | |
| | −HECS | +HECS | −HECS | +HECS |
| (a) total number of wells | 96 | 48 | 96 | 48 |
| (b) number of wells containing growing hybrids | 28 | 38 | 2 | 3 |
| % = $\frac{b}{a}$ × 100 | 29% | 79% | 2% | 6% |

TABLE B

| | mouse myeloma cells × human lymphocytes | | | | | | | |
|---|---|---|---|---|---|---|---|---|
| | Fusion 1 | | Fusion 2 | | Fusion 3 | | Fusion 4 | |
| | −HECS | +HECS | −HECS | +HECS | −HECS | +HECS | −HECS | +HECS |
| (a) | 96 | 48 | 96 | 48 | 96 | 96 | 48 | 48 |
| (b) | 0 | 36 | 15 | 17 | 1 | 6 | 1 | 5 |
| % | 0 | 75% | 16% | 35% | 1% | 6% | 2% | 10% |

The data show that "HECS" induce constantly a higher number of hybrids after fusion of both mouse and human lymphocytes.

EXAMPLE 3

Increase of cloning efficiency by limiting dilution induced by endothelial cells or "HECS".

To obtain growth of a single hybridoma cell, feeder cells are needed.

Hybridoma cells obtained after fusion are collected and dispensed in wells at three different concentrations (5 hybridomas/well; 1 hybridoma/well; 0.5 hybridoma/well in the presence of different feeder cells. The following table C illustrates the efficiency of human endothelial cells compared with other cells commonly used as feeder cells:

TABLE C

| | number of hybridomas/well | | |
|---|---|---|---|
| feeder cells | 5 | 1 | 0.5 |
| medium alone | 0/36 | 0/36 | 0/24 |
| mouse spleen cells | 24/36 | 7/36 | 3/24 |
| human fibroblast | 13/36 | 6/36 | 5/24 |
| human endothelial cells | 36/36 | 24/36 | 13/24 |

Results are expressed as number of clones growing/number of wells.

These data show that endothelial cells provide the highest efficiency for the growth of hybridoma clones when used as feeder cells.

The following table D illustrates that feeder cells may be substituted by factor(s) produced in the supernatant of endothelial cells (HECS"). Control "factor" is the medium used to cultivate endothelial cells.

TABLE D

| | number hybridomas/well | | |
|---|---|---|---|
| Factor(s) | 5 | 1 | 0.5 |
| medium alone | 0/36 | 0/36 | 0/24 |
| 1% control "factor" | 0/36 | 0/36 | 0/24 |
| 5% control "factor" | 0/36 | 0/36 | 0/24 |
| 20% control "factor" | 0/36 | 0/36 | 0/24 |
| 1% "HECS" | 2/36 | 0/36 | 0/24 |
| 5% "HECS" | 23/36 | 15/36 | 7/24 |
| 20% "HECS" | 30/36 | 17/36 | 9/24 |

Results are expressed as number of clones growing/total number of wells.

The data of Table D indicate that "HECS" can substitute feeder cells and that the factor is still active at a dilution of 1/20.

EXAMPLE 4

Prolonged survival and stability of mouse/human hybridomas by human endothelial cells.

Mouse/human hybridomas are often very unstable: they rapidly lose the capacity to produce human immunoglobulins and they die. We investigated the best conditions for prolonging their survival, keeping them in culture over two different feeder cells: spleen cells (which are the most commonly used as feeder cells) and human endothelial cells.

Mouse/human hybridomas were kept in culture over mouse spleen cells and human endothelial cells. Cell survival and capacity to produce human immunoglobulins (Ig) was checked every week by microscopical analysis and ELISA technique.

The following Table E illustrates the capacity to prolong human hybridomas survival and stability in producing human Ig by human endothelial cells.

TABLE E

| weeks after the appearance of colonies of hybrids | "Feeder" cells | | | |
|---|---|---|---|---|
| | endothelial cells | | spleen cells | |
| | alive clone/total wells | Ig producing clone/total wells | alive clone/total wells | Ig producing clone/total wells |
| 3 | 12/12 | 11/12 | 12/12 | 11/12 |
| 4 | 12/12 | not done | 6/12 | not done |
| 5 | 12/12 | 11/12 | 0/12 | 2/12 |
| 6 | 12/12 | 11/12 | 0/12 | 0/12 |
| 7 | 12/12 | 4/12 | 0/12 | 0/12 |
| 8 | 12/12 | 4/12 | 0/12 | 0/12 |

These data indicate that endothelial cells prolong the survival and stability in Ig production of human hybridomas.

EXAMPLE 5

Endothelial cell supernatant contains $\pm 2 \times 10^{-8}$M $PGE_2$. We investigated whether the activity of endothelial cell supernatant on the growth of hybridoma cells may be due to the presence of prostaglandins. Since prostaglandins are known to be very unstable when kept at 37° C. at pH higher than 9 for one hour, we incubated the endothelial cell supernatant for 2 h. at 37° C. at different pH. The endothelial cell supernatant was then readjusted at its original pH (pH 7.2) and used to promote the hybridomas growth in limiting dilution.

The following Table F illustrates the stability of endothelial cell supernatant at different pH.

TABLE F

| Feeder cells | number of hybridomas/well | | |
|---|---|---|---|
| | 5 | 1 | 0.5 |
| medium alone | 5/36 | 2/36 | 1/24 |
| 20% endo sup. +4° C. pH 7.2 2h. | 32/36 | 21/36 | 11/24 |
| 20% endo sup. 37° C. pH 7.2 2h. | 33/36 | 23/36 | 10/24 |
| 20% endo sup. 37° C. pH 5.5 2h. | 34/36 | 15/36 | 12/24 |
| 20% endo sup. 37° C. pH 9.1 2h | 36/36 | 19/36 | 4/24 |

Results are expressed as number of clones growing/total number of wells.

These data show that high pH does not abolish endothelial cell supernatant activity, therefore it is unlikely that its activity is only due to prostaglandins.

EXAMPLE 6

Increase of human bone marrow colony forming cells (CFU-C) by human endothelial cell supernatant.

Human bone marrow cells were obtained from healthy donors and cultured in vitro by the method of G. Wagemaker et al. Experimental Hematology Today, eds. S. J. Baum and G. D. Ledney, Springer Verlag, New York, p. 103 (1977).

After 12 days growth of colonies was determined by microscopic analysis. The human endothelial supernatant was used to increase the number of colonies. The following chart illustrates the results.

TABLE G

| | Exp. 1 | Exp. 2 | |
|---|---|---|---|
| | $1 \times 10^5$ bone marrow cells/ml. | $1 \times 10^5$ | $2 \times 10^5$ |
| | | bone marrow cells per ml | |
| −HECS | $28/10^5$ | $0/10^5$ | $22/10^5$ |
| +12.5% HECS | $44/10^5$ | $37/10^5$ | $91/10^5$ |
| +25% HECS | $51/10^5$ | $64/10^5$ | $79/10^5$ |

Results are expressed as numbers of colonies (>40 cells/colony) per 100,000 bone marrow cells.

The data show that endothelial cell supernatant enhance the number of bone marrow colonies, obtained using both 100,000 cells per culture and 200,000 cells/culture.

We claim:

1. A method for improving the hybridization of different, hybridoma forming cells in an in-vitro culture and for increasing the production of substances formed by the resulting hybridomas, which comprises; culturing hybridomas adding to the culture at least one of endothelial cells or the supernatant of endothelial cells.

2. The method of claim 1 wherein the endothelial cells are human cells.

3. The method of claim 2 wherein the additive is supernatant.

4. A method for increasing the production of monoclonal antibodies by monoclonal antibody producing hybridomas in an in-vitro culture of said hybridomas, which comprises; culturing hybridomas adding to the culture at least one of endothelial cells or the supernatant of endothelial cells.

5. The method of claim 4 wherein the endothelial cells are human cells.

6. The method of claim 5 wherein the additive is supernatant.

7. The method of claim 4 wherein the hybridomas are the product of myeloma cell line cells fused with lymphocytes obtained from animals which were immunized with antigens appropriate for the production of said antibodies.

8. In a process for the production of monoclonal antibodies by culturing in-vitro an antibody producing hybridoma under antibody producing conditions, the improvement which comprises; employing as one of said conditions the presence of a production enhancing factor obtained from the in-vitro culture of an endothelial cell.

9. The process of claim 8 wherein the endothelial cell is a human cell.

10. In an in-vitro process for preparing an antibody producing hybridoma by fusion of a myeloma cell with an antibody-producing lympoid cell under conditions promotive of the fusion, the improvement which comprises; employing as one of said conditions the presence of a fusion enhancing factor obtained from the in-vitro culture of an endothelial cell.

11. The process of claim 10 wherein the endothelial cell is a human cell.

12. In a method of culturing human bone marrow cells in-vitro under conditions promoting the growth of the culture colony, the improvement which comprises; employing as one of said conditions the presence of a colony growth promoting factor obtained from in-vitro culturing human endothelial cells.

13. The method of claim 7, characterized in that as hybridoma culture a culture is used which is obtained by fusion of myeloma cell line cells and lymphocytes, derived from animals or human beings, which are immunized with the desired antigens.

* * * * *